(12) United States Patent
Li et al.

(10) Patent No.: US 9,938,522 B2
(45) Date of Patent: Apr. 10, 2018

(54) HIGH THROUGHPUT SEQUENCING OF END REGIONS OF LONG LINEAR DNAS

(71) Applicant: Genewiz, Inc., South Plainfield, NJ (US)

(72) Inventors: Shihong Li, Berkeley Heights, NJ (US); Narisra Jongkam, Highland Park, NJ (US); Ruqin Kou, Princeton, NJ (US); Hairong Duan, Suzhou (CN); Zhenzhen Zhou, Madison, NJ (US); Shifang Zhang, New York, NY (US)

(73) Assignee: GENEWIZ, INC., South Plainfield, NJ (US)

( * ) Notice: Subject to any disclaimer, the term of this patent is extended or adjusted under 35 U.S.C. 154(b) by 227 days.

(21) Appl. No.: 14/865,234

(22) Filed: Sep. 25, 2015

(65) Prior Publication Data

US 2016/0090590 A1    Mar. 31, 2016

Related U.S. Application Data

(60) Provisional application No. 62/055,153, filed on Sep. 25, 2014.

(51) Int. Cl.
*C12Q 1/68* (2006.01)
*C12P 19/34* (2006.01)
*C12N 15/10* (2006.01)

(52) U.S. Cl.
CPC .............................. *C12N 15/1037* (2013.01)

(58) Field of Classification Search
None
See application file for complete search history.

(56) References Cited

U.S. PATENT DOCUMENTS

| | | | |
|---|---|---|---|
| 7,776,532 B2 | 8/2010 | Gibson et al. |
| 9,080,210 B2 | 7/2015 | Van Eijk et al. |
| 2005/0037358 A1 | 2/2005 | Muyldermans |
| 2007/0037196 A1 | 2/2007 | Gibson et al. |
| 2010/0035768 A1 | 2/2010 | Gibson et al. |
| 2015/0232835 A1 | 8/2015 | Watt et al. |
| 2015/0239981 A1 | 8/2015 | Baehner et al. |
| 2015/0246970 A1 | 9/2015 | Dreier et al. |

OTHER PUBLICATIONS

Fullwood et al., "Next-generation DNA sequencing of paired-end tags (PET) for transcriptome and genome analyses," Genome Research, 2009, vol. 19, pp. 521-532.*
Gibson et al., "Enzymatic assembly of DNA molecules up to severla hundred kilobases," Nature Methods (May 2009): 6(5):343-345.

* cited by examiner

*Primary Examiner* — Young J Kim
(74) *Attorney, Agent, or Firm* — Scully Scott Murphy & Presser

(57) ABSTRACT

This invention relates to linking, amplifying and sequencing of two ends of long linear DNAs. In particular, this invention provides methods for pairing and sequencing VH and VL genes that encode two parts of one immunoglobulin. The method of the present invention can be applied to rapid antibody discovery and engineering.

19 Claims, 6 Drawing Sheets

Step1: Add palindromic fusion adaptor by PCR or ligation

Step2: Circularization and Removal of Linear DNA

*Step2b: Optional RCA*

Step3: PCR (multiplex or pool of individual)

To Amplify linked LV (forward) and HV (reverse complement)

To add Ilumina adaptor

Step4: 2*300bp Miseq

Step5: Data analysis

FIG 4

HIGH THROUGHPUT SEQUENCING OF END REGIONS OF LONG LINEAR DNAS

CROSS REFERENCE TO RELATED APPLICATION

This application claims priority to U.S. Provisional Application No. 62/055,153 filed on Sep. 25, 2014. The content of the application is incorporated herein by reference in its entirety.

FIELD OF THE INVENTION

This invention relates generally to high throughput nucleic acid sequencing of two ends of a long linear DNA and related uses.

BACKGROUND OF THE INVENTION

There is a need in the art for sequencing the ends of long linear DNAs for various applications including, e.g., phage-display libraries and many others. Phage-displayed technology has demonstrated to be the most successful technology in producing effective therapeutic antibodies for many diseases and indications. The success of the industry depends on the quality and diversity of the phage-displayed antibody library. The diversity of the library lies in the variable regions of both the heavy chain and light chain.

In a typical phage-displayed antibody library, the VH (heavy chain variable region) and VL (light chain variable) are separated from each other by a long stretches of sequences encoding the constant regions (CH1 or CL), phage coat proteins, and secreting signals. Traditionally, Sanger sequencing were performed to sample the diversity of the library or verify the sequence of the selected clones after repeated panning. Using Sanger sequencing, both heavy chain and light chain variable region can be read but only limited number of the clones can be assessed due to the low throughput. With high throughput parallel sequencing, a vast population of the library could be read. However, with today's technology, it remains challenging to sequence both the heavy chain and light chain variable at same time. There is a need to sequence the VH and VL DNA sequence together as they are paired in the phage-display construct.

SUMMARY OF INVENTION

This invention relates to high throughput nucleic acid sequencing of two ends of a long linear target DNA and related uses.

One aspect of this invention provides a method for obtaining sequence identities of two end segments of a linear double stranded DNA (dsDNA) molecule. The method includes providing a dsDNA molecule containing (1) a 5' end segment at the 5' end of the dsDNA molecule and (2) a 3' end segment at the 3' end of the dsDNA molecule, the two end segments being separated by a spacer segment; fusing the two end segments to form a circular dsDNA molecule and a joined section on the dsDNA molecule that has the two end segments joined by a junction, and sequencing the joined section (e.g., using high throughput sequencing) thereby obtaining the sequence identities of the two end segments. In one example, the two end segments can encode an immunoglobulin heavy chain variable region and an immunoglobulin light chain variable region respectively. The spacer can be of any length (e.g., 100 bp, 200 bp, 300 bp, 500 bp, 1 kb, 2 kb, 5 kb, 10 kb, 20 kb, 50 kb, and 100 kb.)

In particular, this invention provides a method for obtaining sequence identities of a plurality of clones of a phage-displayed antibody library, comprising, (i) providing plurality of linear double stranded DNA (dsDNA) molecules from said clones, each dsDNA molecule containing (1) a 5' end segment at the 5' end of the dsDNA molecule and (2) a 3' end segment at the 3' end of the dsDNA molecule, the two end segments being separated by a spacer segment; (ii) Fusing the two end segments to form a circular dsDNA molecule and a joined section on the dsDNA molecule that has the two end segments joined by a junction, and (iii) sequencing the joined section of each dsDNA molecule from each clone using high throughput sequencing thereby obtaining the sequence identities of the plurality of clones.

In the method, the fusing step can be carried out by a process comprising: joining each of the 5' and 3' ends of the dsDNA molecule with an adaptor; and incubating the dsDNA molecule under conditions permitting annealing of the two ends via a sequence of the adaptor. The adaptor can be selected from the group consisting of a palindromic adaptor having a palindromic sequence, a U-containing adaptor, and a loxP adaptor. The adaptor can be added to the two ends of the dsDNA molecule by ligation or via PCR. For example, one can ligate or PCR to add U-containing Adaptor, treat with USER (Uracil-Specific Excision Reagent) Enzyme, a mixture of Uracil DNA glycosylase (UDG) and the DNA glycosylase-lyase Endonuclease VIII, to create sticky ends, ligate the sticky ends with ligase. Alternatively, one can ligate or PCR to add a loxP adaptor to each end, and circularize the linear dsDNA with a Cre recombinase. The above-mentioned palindromic sequence can be about 10-50 bp, e.g., 15, 20, 25, 30, 35, 40, 45, or 50 bps long. It can have a Tm of about 50° C. The fusing step and adaptor adding step can be carried out at 50° C. in presence of: (i) an exonuclease for generating complementary single strand overhang at each end, (ii) a polymerase to fill in a gap after overhangs at the ends hybridize to each other, and (iii) a ligase to seal a nick.

Before the sequencing step, the above-described method can further include fragmenting the circular dsDNA molecule to generate fragments of a pre-determined size, and selecting fragments containing the two end segments, which have been joined by the junction or circularization linker. In preferred embodiments, before the sequencing step, the method can also include amplifying the joined section to generate an amplicon. In that case, the amplification can be conducted with a forwarding primer annealing to immediately upstream of the 3' end fragment (3' in the original linear version), and a reverse primer anneal to immediately downstream of the 5' end fragment (5' in the original linear version). The forward primer or the reverse primer or both can further have a tag sequence at the 5' end. Examples of the tag sequences include Illumina's P5 and P7 adaptor or partial adaptor. The amplicon can be directly sequenced.

In the method described above, before the sequencing, one can also amplify the circular dsDNA molecule by RCA, which can be carried out using techniques known in the art, e.g., by Phi29 in presence of dNTP and random hexamer or specific primers.

In the method described above, one or more labeled nucleotide triphosphates can be incorporated into the junction in the circular dsDNA molecule. In some embodiments, one or more Biotin-dUTPs can be incorporated at the junction. In that case, the circular dsDNA molecule or a junction-containing section thereof is labeled with biotin and can be selected accordingly, e.g., with streptavidin. In other embodiments, the method described above, before the sequencing step, can further include hybridizing to the joined section with a biotin labeled probe that is complementary to the joined section and isolating the circular dsDNA molecule or a fragment thereof that contains the joined section using one or more streptavidin beads.

The sequencing step of the above-described method can be conducted by any conventional sequencing techniques, including the Sanger method and NGS method.

The details of one or more embodiments of the invention are set forth in the description below. Other features, objectives, and advantages of the invention will be apparent from the description and from the claims.

BRIEF DESCRIPTION OF THE DRAWINGS

FIG. 4 shows steps of an exemplary method of this invention.

DETAILED DESCRIPTION OF THE INVENTION

Figure 1:
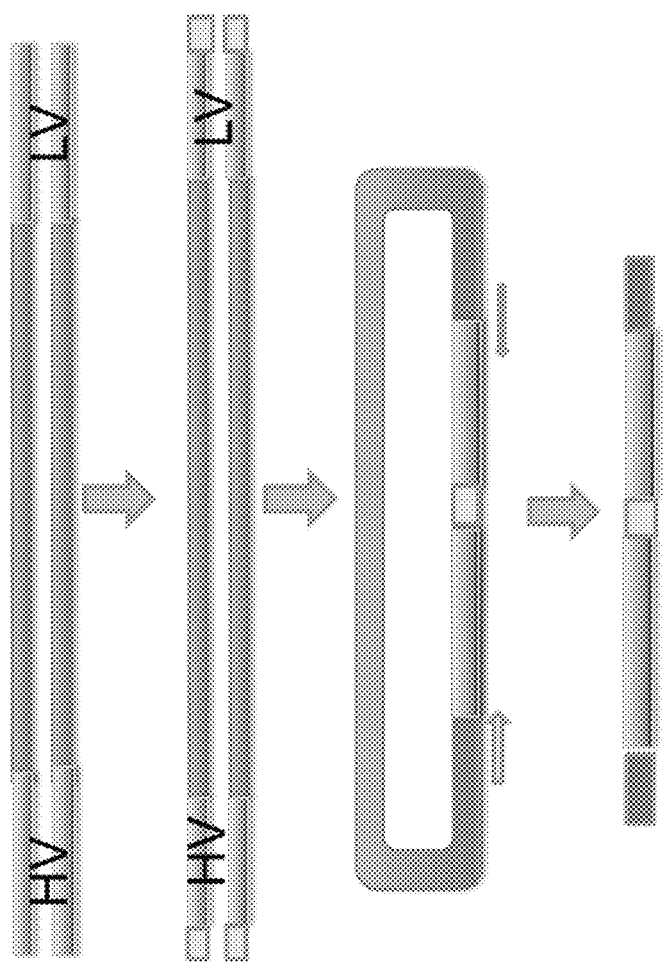
FIG. 1 is a schematic drawing of the principle design of an embodiment of this invention.

This invention provides methods for high throughput nucleic acid sequencing, which can be used in, e.g., antibody discovery and engineering. As disclosed herein, this invention can be used in sequencing phage-displayed antibody library with heavy chain variable region separate from light chain variable by a long stretch of DNA in the same read. The methods of the present invention can be applied to amplification and sequencing of other target DNA or transcripts.

Conventional antibodies are made up of 2 heavy chains and 2 light chains. Each heavy chain contains 1 variable domain and 3 (or 4) constant domains, and each light chain contains 1 variable domain and 1 constant domain. The antigen-binding site is formed by combining the variable domains of light and heavy chains. The variable domain of a light chain, or V-J-REGION, is encoded by two rearranged genes, IGKV and IGKJ for kappa chain, IGLV and IGLJ for lambda chain respectively. The variable domain of a heavy chain, or V-D-J-REGION, is encoded by three rearranged genes, IGHV, IGHD, and IGHJ. To date, in humans, 51 functional VH genes, 25 functional D genes, and 6 functional JH genes have been identified on Chromosome 14q32.3; 40 functional VK genes and 5 functional JK have been identified on Chromosome 2p11-12; 31 functional VL genes and 4 functional LJ genes have been identified on Chromosome 22q11.2. The germ line genes alone will generate 7650 possible heavy chain variable domains and 324 possible light chain variable domains. When multiply by 1000 (to account for the junctional N-diversity and somatic mutation), one can expect $7.6 \times 10^6$ possible heavy chains and $3.5 \times 10^5$ possible light chains. When pair the heavy chain with light chain randomly, one can expect $2.3 \times 10^{12}$ different antibodies.

Much of the diversity lies in the hyper-variable regions called CDR1, 2 and 3. For both heavy chain and light chain, 3 hypervariable regions (or Complementarity Determining Region) called CDR1, CDR2 and CDR3 are separated by 4 frame regions, namely, FR1, FR2, FR3, and FR4. Residues present in CDR1, 2 and 3, on both heavy chain and light chains, particularly HCDR3, are believed to be actively involved in the molecular interaction with the antigen.

One or a few B cells expressing one or a few of the $2.3 \times 10^{12}$ antibodies are bound to display affinity for any antigen encountered. By fusing with a cancer cell, the antibody producing B cell could be immortalized and turn into a factory that manufactures the antibody on demand. The idea first turns into reality in mouse in 1980s and monoclonal antibodies against various antigens are routinely generated in laboratory. One can inject a mouse or a rat or rabbit with any target antigen, isolate B cells, fuse the B cells with a myeloma cell line of corresponding species, and select for the hybridoma cells that produce antibodies with high affinity for the target antigen. The hybridoma cells could be banked or grown indefinitely to churn out monoclonal antibody for the target antigen. The monoclonal antibodies have been invaluable for research, diagnosis and therapy. For therapeutic purpose, however, much more work is needed to humanize the immunoglobulin to avoid adverse reactions triggered by the mouse or rat protein.

The antigen-binding fragment, (Fab)2 or Fab (composed of one variable domain and one constant domain), and single chain variable fragment, scFv (formed by connecting VH and VL with a short linker peptide) retain the specificity of the original immunoglobulin. FAB or scFv with the de novo diversity or CDR-randomized diversity in the context of human frame region could be fused to one of the phage-coat protein, and expressed on phage surface. When panned against a specific antigen, a particular FAB or scFv that bind to the antigen with high affinity will be selectively pulled down while those with low affinity washed off. After several cycles of repeated panning, FAB or scFv with high affinity could be enriched for further characterization.

Whether one succeeds in obtaining a good antibody out of the above process depends, to a great extent, on the quality and particularly the diversity of the library. For difficult antigens such as membrane-bound proteins, the success also depends on the numbers of clones one can afford to sequence. A high throughput sequencing method that can assess both VH and VL simultaneously would both enable library QC and speed up library screening process. This invention provides methods for high throughput nucleic acid sequencing, which can be used in, e.g., antibody discovery and engineering. Shown in FIGS. 1-5 are schematic drawings of the principle and exemplary designs of embodiments of this invention.

Figure 2:
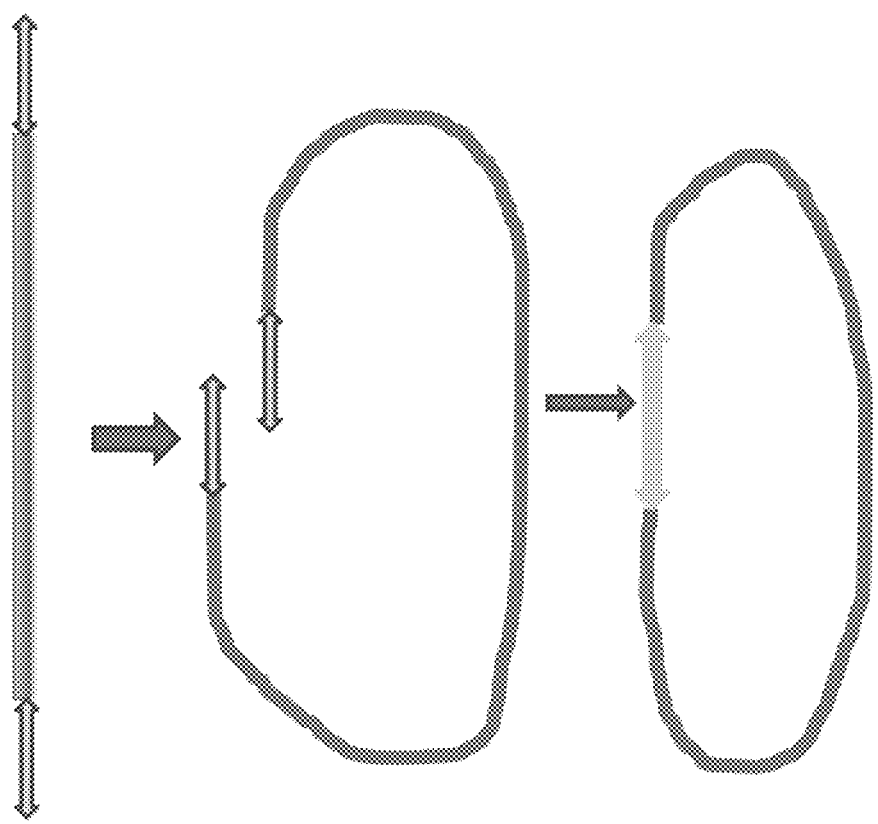
FIG. 2 is a schematic drawing of fusing two ends of a long linear DNA with a palindromic adaptor.
Figure 3:
FIG. 3 shows a schematic drawing of phage-displayed library with VH and VL separated by a long stretch of sequence, which encodes among others antibody constant domain and phage coat proteins.
Figure 5:
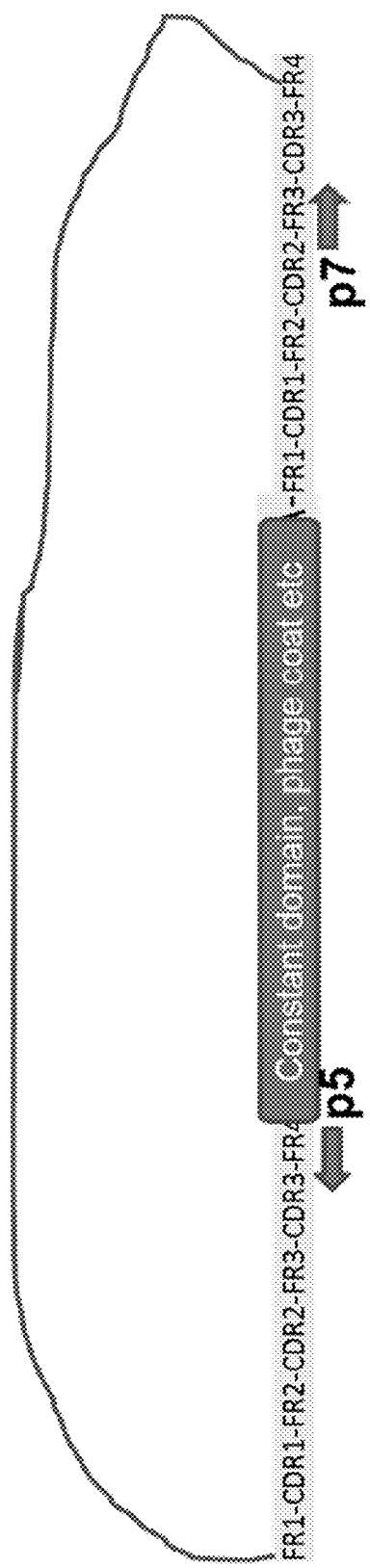
FIG. 5 shows another schematic drawing of phage-displayed library with VH and VL separated by a long stretch of sequence encoding among others antibody constant domain and phage coat proteins.

More specifically, a method disclosed in this invention involves fusing two ends of a long, linear DNA molecule as shown in FIGS. 1-2. It could be adapted and applied to therapeutic antibody discovery research, particularly deep sequencing of phage-displayed antibody library. In one embodiment, a scheme was designed to fuse the VH and VL in cis covalently, and sequence both in the same read and in high efficiency. For example, as shown in FIGS. 2 and 4, palindromic adaptors (arrows) are added to the two ends of the linear DNA by, e.g., PCR or ligation. The DNA is then circularized (see e.g., FIGS. 2 and 5) and any remaining linear DNA is removed. Optionally, RCA can be carried out to amplify the circularized DNA. Then, PCR (multiplex or pool of individual) can be carried out to amplify linked LV (forward) and HV (reverse complement) using PCR primers (the inner, smaller arrows shown in FIG. 3 and the arrows shown in FIG. 5) and to add adaptors (e.g., Ilumina p5 and p7, which are incorporated by reference). As shown in FIGS. 3 and 5, the PCR primers can be designed based on a frame region (e.g., FR1, FR2, FR3 or FR4) of a heavy chain or light chain based on the need of an investigator. The PCR products are subjected to DNA sequencing such as 2×300 bp sequence on Miseq and the sequencing data can be analyzed according to methods known in the art.

The method disclosed herein can be employed to QC the library, particularly to assess the diversity of the library, and to identify antigen-specific enrichment especially early in the panning process or in presence of high background such as in cases when the antigen displayed are membrane bound or expressed on cell surface in background of other surface proteins.

To that end, the method disclosed in this invention is a key aspect of processes for the production of high affinity antigen binding polypeptides, and specifically monoclonal antibodies, against a target antigen of interest. Such a process generally includes (a) determining the nucleotide sequence encoding at least one hypervariable loop or CDR of the VH and/or the VL domain of an antibody immune-reactive with the target antigen; and (b) expressing an antigen binding polypeptide immune-reactive with said target antigen, said antigen binding polypeptide comprising a VH and a VL domain, wherein at least one hypervariable loop or CDR of the VH domain or the VL domain has an amino acid sequence encoded by the nucleotide sequence determined in part (a).

The first step of the process may involve active immunization of a suitable animal, such as a mouse, a rat, a rabbit, a sheep, or a species in the family Camelidae in order to elicit an immune response against the target antigen, thereby raising conventional antibodies immunoreactive with the target antigen. Protocols for immunization of such animals are well known in the art and described e.g., US20150246970 and US 20050037358. The antigen preparation used for immunization may be a purified form of the target antigen, for example recombinantly expressed polypeptide, or an immunogenic fragment thereof. However, it is also possible to immunize with crude preparations of the antigen, such as like isolated cells or tissue preparations expressing or encoding the target antigen, cell lysates, cell supernatants or fractions such as cell membranes, etc., or with a polynucleotide encoding said target antigen (a DNA immunization).

Following active immunization with the target antigen, peripheral blood lymphocytes or biopsies such as lymph nodes or spleen biopsies may be isolated from the immunized animal, immortalized (by cell fusion to form hybridoma cells) and screened for production of conventional antibodies against the target antigen. Techniques such as enrichment using panning or FACS sorting may be used at this stage to reduce the complexity of the B cell or hybridoma cell repertoire to be screened. Antigen-specific B or hybridoma cells are then selected and used for total RNA extraction and subsequent cDNA synthesis. Nucleic acid encoding the native VH and VL domains (specific for the target antigen) can be isolated by PCR.

It is not essential to use active immunization in order to identify convention antibodies immunoreactive with a target of interest. For example, it is possible to make use of an animal's (a non-human animal's or a human being's) own immune response, either the immunodiversity naturally present in the animal, or for example a diseased animal or animal which has been naturally exposed to a particular pathogen, e.g. by normal infection routes. In this regard, the invention encompasses the use of non-immune libraries. If "natural" immune responses within the animal already give rise to antibodies which bind the target antigen of interest, then it is possible to make use of the genetic engineering techniques and other standard techniques known in the art, in order to culture and isolate B cells producing such antibodies, or produce monoclonal cultures of such antibodies, and/or to determine the nucleotide sequence of the gene segments encoding the VH and/or VL domains of such antibodies. Armed with this sequence information, it is then possible to engineer recombinant DNA constructs encoding antigen binding polypeptides which embody the derived VH and/or VL, or the hypervariable loops (or CDRs) thereof.

Nucleic acid encoding VH and VL domains (whether obtained by active immunization or by other means) may be cloned directly into an expression vector for the production of an antigen binding polypeptide according to techniques known in the art (e.g., US20150246970, US20150232835, US 20150239981, and US 20050037358). In particular, these sequences could be cloned into an expression vector which also encodes a human antibody constant region, or a portion thereof, in order to produce a chimeric antibody. However, it is typical to carry out further manipulations on the isolated VH and VL sequences before cloning and expression with human constant region sequences.

As a first step, candidate VH and VL sequences (including sequences isolated following the active immunization) from the animal may be used to prepare a library (e.g. Fab libraries). The library may then be screened (e.g. using phage display) for binding to the target antigen. Promising lead candidates can be further tested for target antigen binding, for example using Biacore or a suitable bioassay. Finally, the sequences encoding the VH and VL domains of the most promising leads can be cloned as an in-frame fusion with sequences encoding a human antibody constant region.

It is not essential that the polynucleotide sequence used to encode the animal-derived hypervariable loops (HVs)/CDRs (e.g. for recombinant expression of the antigen binding polypeptide of the invention) is identical to the native polynucleotide sequence which naturally encodes the HVs/CDRs in the animal. For example, one can conduct codon optimization, and other changes in polynucleotide sequence related to cloning and/or expression, which do not alter the encoded amino acid sequence, according to techniques known in the art.

As disclosed herein, this invention can be used in sequencing phage-displayed antibody library with heavy chain variable region separate from light chain variable by a long stretch of DNA. A variety of methods are known in the art for generating phage display libraries and screening such libraries for antibodies possessing the desired binding characteristics. Such methods are reviewed in, e.g., Hoogenboom, H. R., et al., in Methods in Molecular Biology 178 (2002) 1-37 (O'Brien et al., ed., Human Press, Totowa, N.J., 2001) and further described, e.g., in the McCafferty, J., et al., Nature 348 (1990) 552-554; Clackson, et al., Nature 352 (1991) 624-628; Marks, et al., J. Mol. Biol. 222 (1992)

581-597; Marks, and Bradbury, in Methods in Molecular Biology 248 161-175 (Lo, ed., Human Press, Totowa, N.J., 2003); Sidhu, et al., J. Mol. Biol. 338(2) (2004) 299-310; Lee, et al., J. Mol. Biol. 340(5) (2004) 1073-1093; Fellouse, Proc. Natl. Acad. Sci. USA 101(34) (2004) 12467-12472; and Lee, et al., J. Immunol. Methods 284(1-2) (2004) 119-132.

In certain phage display methods, repertoires of VH and VL genes are separately cloned by polymerase chain reaction and recombined randomly in phage libraries, which can then be screened for antigen-binding phage as described in Winter, et al., Ann. Rev. Immunol., 12 (1994) 433-455. Phage typically display antibody fragments, either as single-chain Fv (scFv) fragments or as Fab fragments. Libraries from immunized sources provide high-affinity antibodies to the immunogen without the requirement of generating hybridomas. Alternatively, the naive repertoire can be cloned (e.g., from human) to provide a single source of antibodies to a wide range of non-self and also self-antigens without any immunization as described by Griffiths, et al., EMBO J, 12 (1993) 725-734. Finally, naive libraries can also be made synthetically by cloning un-rearranged V-gene segments from stem cells, and using PCR primers containing random sequence to encode the highly variable CDR3 regions and to accomplish rearrangement in vitro, as described by Hoogenboom, and Winter, J. Mol. Biol., 227 (1992) 381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments can be isolated from antibody phage libraries generated using the techniques described in McCafferty et al., Nature 348 (1990) 552-554. Clackson, et al., Nature 352 (1991) 624-628 and Marks, et al., J. Mol. Biol. 222 (1991) 581-597 describe the isolation of murine and human antibodies, respectively, using phage libraries. Subsequent publications describe the production of high affinity (nM range) human antibodies by chain shuffling (Marks, et al., Bio/Technology 10 (1992) 779-783), as well as combinatorial infection and in vivo recombination as a strategy for constructing very large phage libraries (Waterhouse, et al., Nuc. Acids. Res. 21 (1993) 2265-2266). These techniques are alternatives to traditional monoclonal antibody hybridoma techniques for isolation of monoclonal antibodies.

Library screening/selection typically involves contacting expression products encoded by clones in the library (i.e., VH/VL pairings in the form of antigen binding polypeptides, e.g. Fabs, scFVs or antibodies) with a target antigen, and selecting one or more clones which encode a VH/VL pairings exhibiting the desired antigen binding characteristics.

Phage display libraries may be selected on immobilized target antigen or on soluble (often biotinylated) target antigen. The Fab format allows affinity driven selection due to its monomeric appearance and its monovalent display on phage, which is not possible for scFv (as a consequence of aggregation and multivalent display on phage) and IgG (bivalent format). Two to three rounds of selections are typically needed to get sufficient enrichment of target specific binders. Affinity driven selections can be performed by lowering the amount of target antigen in subsequent rounds of selection, whereas extended washes with non-biotinylated target enables the identification of binders with extremely good affinities.

The selection procedure allows the user to home in on certain epitopes; whereas the classical method for elution of phage clones from the immobilized target is based on a pH shock, which denatures the antibody fragment and/or target, competition with a reference mAb against the target antigen or soluble receptor or cytokine leads to the elution of phage displaying antibody fragments binding to the relevant epitope of the target (this is of course applicable to other display systems as well, including the B cells selection method).

Individual clones taken from the selection outputs may be used for small scale production of antigen-binding polypeptides (e.g. antibody fragments) using periplasmic fractions prepared from the cells or the culture supernatants, into which the fragments "leaked" from the cells. Expression may be driven by an inducible promoter (e.g. the lac promoter), meaning that upon addition of the inducer (IPTG) production of the fragment is initiated. A leader sequence ensures the transport of the fragment into the periplasm, where it is properly folded and the intramolecular disulfide bridges are formed.

The resulting crude protein fractions may be used in target binding assays, such as ELISA. For binding studies, phage prepared from individual clones can be used to circumvent the low expression yields of Fabs, which in general give very low binding signals. These protein fractions can also be screened using in vitro receptor-ligand binding assays to identify antagonistic antibodies; ELISA based receptor-ligand binding assays can be used, also high throughput assays like Alphascreen are possible. Screening may be performed in radio-labelled ligand binding assays, in which membrane fractions of receptor overexpressing cell lines are immobilized; the latter assay is extremely sensitive, since only picomolar amounts of radioactive cytokine are needed, meaning that minute amounts of antagonistic Fabs present in the crude protein fraction will give a positive read-out. Alternatively, FACS can be applied to screen for antibodies, which inhibit binding of a fluorescently labelled cytokine to its receptor as expressed on cells, while FMAT is the high throughput variant of this.

Fabs present in periplasmic fractions or partially purified by IMAC on its hexahistidine tag or by protein G (known to bind to the CH1 domain of Fabs) can be directly used in bioassays using cells, which are not sensitive to bacterial impurities; alternatively, Fabs from individual E. coli cells can be recloned in mammalian systems for the expression of Fabs or IgG and subsequently screened in bioassays.

Following identification of positive expression vector clones, i.e. clones encoding a functional VH/VL combination which binds to the desired target antigen, one can then determine the nucleotide sequences of the variable regions, and hence deduce the amino acid sequences of the encoded VH and VL domains. As shown in the examples below, the sequencing strategies disclosed hereon allow one to obtain the sequence information more accurately in a faster, high throughput manner.

The VH and VL-encoding gene segments of selected expression clones encoding VH/VL pairings exhibiting desirable antigen-binding characteristics (e.g. phage clones encoding scFVs or Fabs) may be subjected to downstream processing steps and re-cloned into alternative expression platforms, such as vectors encoding antigen binding polypeptide formats suitable for human therapeutic use (e.g. full length antibodies with fully human constant domains).

The term "nucleic acid" as used herein refers to a DNA molecule (e.g., a genomic DNA or cDNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. A nucleic acid adapter of this invention can include canonical and/or non-canonical nucleic acid bases. The term "canonical" is used to refer to the four common nucleic acid bases adenine, cytosine, guanine and thymine that are commonly found in DNA or to the respective deoxyribonucleosides, deoxyribonucleotides or 2'-deoxyribonucleoside-5'-triphosphates that contain a canonical base. The term "non-canonical" is used to refer to nucleic acid bases in DNA other than the four canonical bases, or to the respective deoxyribonucleosides, deoxyribonucleotides, or 2'-deoxyribonucleoside-5'-triphosphates that contain a non-canonical base. For example, although uracil is a common nucleic acid base in RNA, uracil is a non-canonical base in DNA. "Non-canonical bases" are found in nucleic acids as a result of incorporation of non-canonical nucleotides (e.g., by synthesis using an oligonucleotide synthesizer or by synthesis using a DNA polymerase) or as a result of modification of existing bases (canonical or non-canonical).

"Sequencing" refers to determining the order of nucleotides (base sequences) in a nucleic acid sample, e.g. DNA or RNA. Many techniques are available such as Sanger sequencing and High Throughput Sequencing technologies (HTS). Sanger sequencing may involve sequencing via detection through (capillary) electrophoresis, in which up to 384 capillaries may be sequence analysed in one run. High throughput sequencing involves the parallel sequencing of thousands or millions or more sequences at once. HTS can be defined as Next Generation sequencing, i.e. techniques based on solid phase pyrosequencing or as Next-Next Generation sequencing based on single nucleotide real time sequencing (SMRT). HTS technologies are available such as offered by Roche, Illumina and Applied Biosystems (Life Technologies). Further high throughput sequencing technologies are described by and/or available from Helicos, Pacific Biosciences, Complete Genomics, Ion Torrent Systems, Oxford Nanopore Technologies, Nabsys, ZS Genetics, GnuBio. Each of these sequencing technologies has their own way of preparing samples prior to the actual sequencing step. These steps may be included in the high throughput sequencing method. In certain cases, steps that are particular for the sequencing step may be integrated in the sample preparation protocol prior to the actual sequencing step for reasons of efficiency or economy. For instance, adapters that are ligated to fragments may contain sections that can be used in subsequent sequencing steps (so-called sequencing adapters). Or primers that are used to amplify a subset of fragments prior to sequencing may contain parts within their sequence that introduce sections that can later be used in the sequencing step, for instance by introducing through an amplification step a sequencing adapter or a capturing moiety in an amplicon that can be used in a subsequent sequencing step. Depending also on the sequencing technology used, amplification steps may be omitted.

An "adapter" is a short double-stranded DNA molecule with a limited number of base pairs, e.g. about 10 to about 100 base pairs in length, which are designed such that they can be ligated to the ends of DNA fragments or amplicons. Adapters are generally composed of two synthetic oligonucleotides which have nucleotide sequences which are at least partially complementary to each other. An adapter may have blunt ends, may have staggered ends, or a blunt end and a staggered end. A staggered end is a 3' or 5' overhang. When mixing the two synthetic oligonucleotides in solution under appropriate conditions, they will anneal to each other forming a double-stranded structure. After annealing, one end of the adapter molecule may be designed such that it is compatible with the end of a restriction fragment and can be ligated thereto; the other end of the adapter can be designed so that it cannot be ligated, but this does need not to be the case, for instance when an adapter is to be ligated in between DNA fragments. In certain cases adapters can be ligated to fragments to provide for a starting point for subsequent manipulation of the adapter-ligated fragment, for instance for amplification or sequencing. In the latter case, so-called sequencing adapters may be ligated to the fragments.

As used herein, a "tag" refers to a non-target nucleic acid component, generally DNA, which provides a means of addressing a nucleic acid fragment to which it is joined. For example, in preferred embodiments, a tag comprises a nucleotide sequence that permits identification, recognition, and/or molecular or biochemical manipulation of the DNA to which the tag is attached (e.g., by providing a site for annealing an oligonucleotide, such as a primer for extension by a DNA polymerase, or an oligonucleotide for capture or for a ligation reaction). The process of joining the tag to the DNA molecule is sometimes referred to herein as "tagging" and DNA that undergoes tagging or that contains a tag is referred to as "tagged" (e.g., "tagged DNA"). A "tag portion" or a "tag domain" means a portion or domain of a tag that exhibits a sequence for a desired intended purpose or application.

As used herein, a "sequencing tag" or a "sequencing tag domain" means a tag or tag domain that exhibits a sequence for the purposes of facilitating sequencing of the ssDNA fragment to which the tag is joined using the method to synthesize tagged circular ssDNA fragments (e.g., to provide a priming site for sequencing by synthesis, or to provide annealing sites for sequencing by ligation, or to provide annealing sites for sequencing by hybridization). For example, in some embodiments, the sequencing tag domain provides a site for priming DNA synthesis of said ssDNA fragment or the complement of said ssDNA fragment.

As used herein, an "amplification tag" or "amplification tag domain" means a tag or a tag domain that exhibits a sequence for the purpose of facilitating amplification of a nucleic acid to which said tag is appended. For example, in some embodiments, the amplification tag or domain provides a priming site for a nucleic acid amplification reaction using a DNA polymerase (e.g., a PCR amplification reaction or a strand-displacement amplification reaction, or a rolling circle amplification reaction), or a ligation template for ligation of probes using a template-dependent ligase in a nucleic acid amplification reaction (e.g., a ligation chain reaction).

As used herein, a "detection tag" or a "detection tag domain" means a tag or tag domain that exhibits a sequence or a detectable chemical or biochemical moiety for the purpose of facilitating detection of the tagged ssDNA fragment (e.g., wherein the sequence or chemical moiety comprises or is joined to a detectable molecule; such as a detectable molecule selected from among: a visible, fluorescent, chemiluminescent, or other detectable dye; an enzyme that is detectable in the presence of a substrate, e.g., an alkaline phosphatase with NBT plus BCIP or a peroxidase with a suitable substrate); a detectable protein, e.g., a green fluorescent protein; and an affinity-binding molecule (e.g., biotin) that is bound to a detectable moiety or that can form an affinity binding pair or a specific binding pair with another detectable affinity-binding molecule; or any of the many other detectable molecules or systems known in the art).

As used herein, an "address tag" or an "address tag domain" means a tag or a tag domain that exhibits a sequence that permits identification of a specific sample (e.g., wherein the transferred strand has a different address tag domain that exhibits a different sequence for each sample).

As used herein, a "DNA fragment library" or a "library of DNA fragments" means a collection or population of tagged DNA fragments generated from target DNA, wherein the combination of the tagged DNA fragments in the collection or population exhibits sequences that are qualitatively and/or quantitatively representative of the sequence of the target DNA from which the tagged DNA fragments were generated, and wherein the tagged DNA fragments that are in the collection or population have not been selected for or selected against by intentionally using a method that either includes or excludes tagged DNA fragments based on the nucleotide or sequence composition of the target DNA. For a variety of reasons, it is possible that a DNA fragment library may not contain a tagged DNA fragment representing every sequence which is exhibited by the target DNA.

The term "primer" or "primer oligonucleotide" refers to a strand of nucleic acid or an oligonucleotide capable of hybridizing to a template nucleic acid and acting as the initiation point for incorporating extension nucleotides according to the composition of the template nucleic acid for nucleic acid synthesis. "Extension nucleotides" refer to any nucleotides (e.g., dNTP) capable of being incorporated into an extension product during amplification, i.e., DNA, RNA, or a derivative if DNA or RNA, which may include a label.

The term "oligonucleotide" refers to a short polymer of nucleotides and/or nucleotide analogs. An oligonucleotide is preferably at least 4 nucleotides, e.g., at least about 10-15, 10-20, 15-25, or 15 to 200 nucleotides. The exact size will depend on many factors, which in turn depend on the ultimate function or use of the oligonucleotide. The oligonucleotide may be generated in any manner, including chemical synthesis, DNA replication, reverse transcription, PCR, ligation, or a combination thereof.

The term "probe" as used herein refers to an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled with a label such as with biotin to which a streptavidin complex may later bind.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

As used herein the term "amplification" and its variants includes any process for producing multiple copies or complements of at least some portion of a polynucleotide, said polynucleotide typically being referred to as a "template." The template polynucleotide can be single stranded or double stranded. A template may be a purified or isolated nucleic acid, or may be non-purified or non-isolated. Amplification of a given template can result in the generation of a population of polynucleotide amplification products, collectively referred to as an "amplicon." The polynucleotides of the amplicon can be single stranded or double stranded, or a mixture of both. Typically, the template will include a target sequence, and the resulting amplicon will include polynucleotides having a sequence that is either substantially identical or substantially complementary to the target sequence. In some embodiments, the polynucleotides of a particular amplicon are substantially identical, or substantially complementary, to each other; alternatively, in some embodiments the polynucleotides within a given amplicon can have nucleotide sequences that vary from each other. Amplification can proceed in linear or exponential fashion, and can involve repeated and consecutive replications of a given template to form two or more amplification products. Some typical amplification reactions involve successive and repeated cycles of template-based nucleic acid synthesis, resulting in the formation of a plurality of daughter polynucleotides containing at least some portion of the nucleotide sequence of the template and sharing at least some degree of nucleotide sequence identity (or complementarity) with the template. In some embodiments, each instance of nucleic acid synthesis, which can be referred to as a "cycle" of amplification, includes creating free 3' end (e.g., by nicking one strand of a dsDNA) thereby generating a primer and primer extension steps; optionally, an additional denaturation step can also be included wherein the template is partially or completely denatured. In some embodiments, one round of amplification includes a given number of repetitions of a single cycle of amplification. For example, a round of amplification can include 5, 10, 15, 20, 25, 30, 35, 40, 50, or more repetitions of a particular cycle. In one exemplary embodiment, amplification includes any reaction wherein a particular polynucleotide template is subjected to two consecutive cycles of nucleic acid synthesis. The synthesis can include template-dependent nucleic acid synthesis.

Amplification of this invention includes isothermal amplification. The term "isothermal" means conducting a reaction at substantially constant temperature, i.e., without varying the reaction temperature in which a nucleic acid polymerization reaction occurs. Isothermal temperatures for isothermal amplification reactions depend on the strand-displacing nucleic acid polymerase used in the reactions. Generally, the isothermal temperatures are below the melting temperature (Tm; the temperature at which half of the potentially double-stranded molecules in a mixture are in a single-stranded, denatured state) of the predominant reaction product, i.e., generally 90° C. or below, usually between about 20° C. and 75° C., and preferably between about 30° C. and 60° C., or more preferably at about 37° C.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 50" may indicate a range of 45-55, and "about 1" may mean from 0.9-1.1. Other meanings of "about" may be apparent from the context, such as rounding off, so, for example "about 1" may also mean from 0.5 to 1.4.

Example 1

Figure 6A:
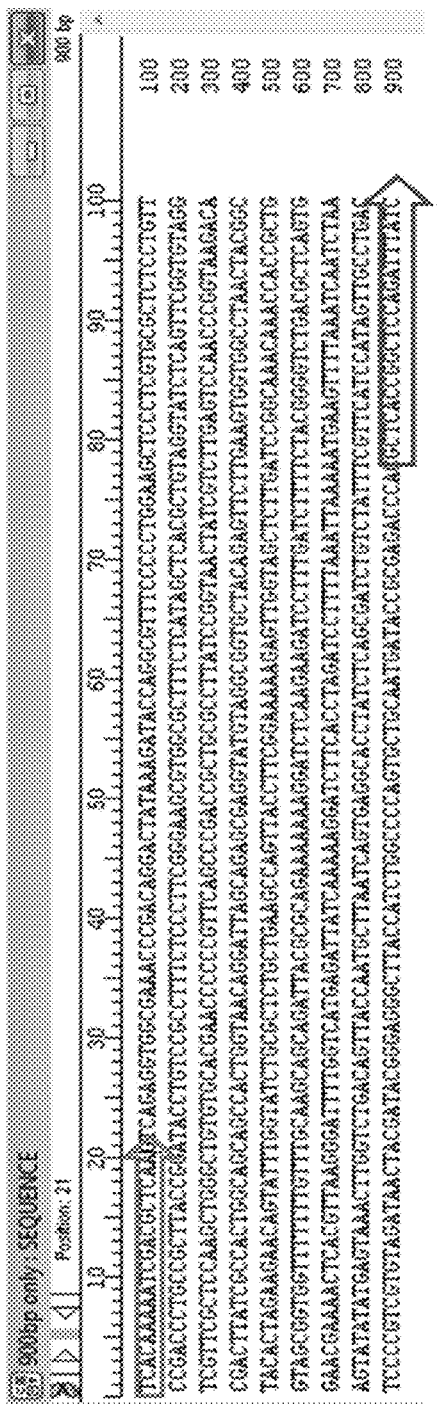
FIG. 6A shows a 900 bp liner DNA fragment (SEQ ID No: 12) that was circularized for sequencing its two end sequences (arrows) in pair.
Figure 6B:
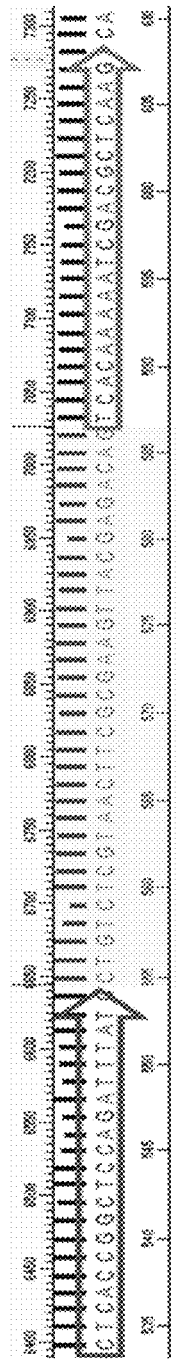
FIG. 6B shows a Sanger sequencing result of the junction region (CTCACCGGCTCCAGATTTATCctgtctcgtaacttcgcgaagttacgagacagTCACAAAAATCGACGC TCAAGTCA, SEQ ID No: 13) of the circularized 900 bp DNA.

In this example, a 900 bp liner DNA fragment (SEQ ID No: 12, see FIG. 6A) was circularized for sequencing its two end sequence in pair. Briefly, a palindromic adaptor, 5'CTGTCTCGTAACTTCGCGAAGTTAC3' (SEQ ID No.: 1) was added to each end of the 900 bp linear DNA (FIG. 1). Then, the adaptor-containing DNA was circularized and the joined section was sequenced. As shown in FIGS. 6A and 6B, it was found that the two ends (arrows in the figures) were efficiently linked as demonstrated by Sanger sequence with an internal primer (850 F: 5' GCAGCCACTGG-TAACAGGAT 3', SEQ ID No.: 2). As shown in FIG. 6B, the internal primer read to the 3' end and continued to read through the linking adaptors and back to the 5' end (SEQ ID No: 13) of the 900 bp DNA.

Example 2

In this example, the method described above was used to sequence DNAs obtained from Fab-phage-displayed libraries.

Briefly, a palindromic fusion adaptor was added to four Fab-phage-displayed libraries via PCR and the resulting libraries were circularized. The VH and VL, now linked together with total length of around 600 bp, were PCR amplified with a mixture of 4 forwarding primers: 5' NNGAA CGC GCG ACC CTG AGC T3', 5' NGGT GAA CGT GCT ACC ATC AAC TGC3'; 5' NNGAA CGC GCG ACC CTG A3'; 5' NGGC GAT CGC GTA ACT ATC ACT TGT 3' (SEQ ID Nos.: 3-6) and one reverse primer: 5'NNACGGTCACCAGGGTGCCCT3' (SEQ ID No.: 7) extended with partial Illumina adaptors P5: 5' AC ACT CTT TCC CTA CAC GAC GCT CTT CCG ATC T (SEQ ID No.: 8) and p7; 5' G ACT GGA GTT CAG ACG TGT GCT CTT CCG ATC T (SEQ ID No.: 9). The resulted amplicon were further amplified to attach index and full adaptor, and subjected to 2×300 bp sequence on Miseq. High quality data were generated in pair and both HCDR3 and LCDR3 were identified in up to 86% of reads. The results are summarized in the tables below.

TABLE 1

| Miseq, 2*300 bp | Fuseq-ab (~600 bp), 7 library/1 run | Conventional (~1250 bp), 4 library/1 run |
|---|---|---|
| total reads/run | 20,643,774 | 6,105,847 |
| Average pared reads/lib | 1,474,555 | 763,230 |
| Read length | 2 × 300 bp | 2 × 300 bp |

TABLE 1-continued

| Miseq, 2*300 bp | Fuseq-ab (~600 bp), 7 library/1 run | Conventional (~1250 bp), 4 library/1 run |
|---|---|---|
| >Q30 (forward reads) | 86.00% | *65.3% |
| >Q30 (reverse reads) | 66.40% | *49.8% |

*The numbers should be lower as they were inflated by leaked in PhiX, which makes up 73-87% of the high quality reads.

TABLE 2a

Paired Fab data from FuzeSeqeq-ab

| | Reads | *HCDR3 identified | LCDR3 identified | Either HCDR3 or LCDR3 identified | *Both LCDR3 and HCDR3 defined |
|---|---|---|---|---|---|
| S1 | 1073637 | *77% | 91% | 97% | 70% |
| S2 | 1233553 | 95% | 91% | 99% | 86% |
| S3 | 1834153 | 89% | 92% | 99% | 82% |
| S4 | 1116267 | 83% | 89% | 97% | 74% |

*The number could be higher if low quality parts were trimmed away before running Igblast. For example, for S1, 87% (instead of 77%) HCDR3 were identified when nucleotides with Q20 were trimmed away from 3' end of the reverse read.

TABLE 2b

Fab data from conventional NGS

| | reads | Either LCDR3 or HCDR3 identified |
|---|---|---|
| S1 | 1458318 | 1.20% |
| S2 | 1043131 | 2.19% |
| S3 | 1217041 | 2.56% |
| S4 | 2387357 | 2.03% |

As shown above, using the method disclosed in this invention, 97%-99% of the sequence reads were found to have sequences of either the HCDR3 or LCDR3. In contrast, using a conventional method, only 1.2% to 2.03% reads were found to have sequences of either the HCDR3 or LCDR3. Clearly, the method disclosed in this invention is much more efficient.

Example 3

In this example, the method described above was used to sequence additional DNAs obtained from Fab-phage-displayed libraries.

As in Example 2 above, the palindromic fusion adaptor was added to three Fab-phage-displayed libraries via PCR and the resulting libraries were circularized. Linear DNAs were removed by plasmid-specific ATP-dependent DNase. In this example, primers 5'G ACT GGA GTT CAG ACG TGT GCT CTT CCG ATC TnnnTGAC-GATTTCACGTCTGGAG3' (SEQ ID No.: 10) and 5'AC ACT CTT TCC CTA CAC GAC GCT CTT CCG ATC TnnnCAGGGTACCTTGACCCCAGT3' (SEQ ID No.: 11) were designed so that the full length VH coding region (see FIG. 5, left arm) and the CDR3 coding region of VL (see FIG. 5, right arm), with total length of around 450 bp, were PCR amplified. The resulted amplicon were further amplified to attach index and full Illumina p5 adaptor (for the VH region) and p7 adaptor (for the VL region), and subjected to 2×300 bp sequence on Miseq. As shown in Table 3 below, higher quality data were generated in pair and all four targeted CDR regions (HCDR1, HCDR2, HCDR3 and LCDR3) were identified in 76-79% of reads. The results are summarized in the tables below.

TABLE 3

|    | LCDR3 | HCDR3 | LCDR3 and HCDR3 | LCDR3, HCDR2 &3 | LCDR3, HCDR1, 2 &3 |
|----|-------|-------|-----------------|-----------------|--------------------|
| S5 | 97.7% | 90.9% | 88.9%           | 86.3%           | 79.4%              |
| S6 | 97.6% | 89.0% | 86.9%           | 84.7%           | 77.6%              |
| S7 | 97.1% | 87.8% | 85.4%           | 83.0%           | 76.9%              |

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A method for obtaining sequence identities of a plurality of clones of a phage-displayed antibody library, comprising, providing plurality of linear double stranded DNA(dsDNA) molecules from said clones, each dsDNA molecule containing (1) a 5' end segment at the 5' end of the dsDNA molecule and (2) a 3' end segment at the 3' end of the dsDNA molecule, wherein the two end segments are separated by a spacer segment and encode an immunoglobulin heavy chain variable region and an immunoglobulin light chain variable region, respectively;

fusing the two end segments to form a circular dsDNA molecule and a joined section on the dsDNA molecule that has the two end segments joined by a junction, and sequencing the joined section of each dsDNA molecule from each clone using high throughput sequencing thereby obtaining the sequence identities of the plurality of clones.

2. The method of claim 1, wherein the fusing step is carried out by a process comprising:

joining each of the 5' and 3' ends of the dsDNA molecule with an adaptor; and incubating the dsDNA molecule under conditions permitting annealing of the two ends via the sequence of the adaptor.

3. The method of claim 2, wherein the adaptor is selected from the group consisting of a palindromic adaptor, aU-containing adaptor, and a loxP adaptor.

4. The method of claim 3, wherein the palindromic sequence is about 20 bps long.

5. The method of claim 3, wherein the palindromic sequence has a Tm of about 50° C.

6. The method of claim 2, wherein the adaptor is added to the two ends of the dsDNA molecule by ligation or via PCR.

7. The method of claim 1, wherein the fusing step is carried out at 50° C. in presence of: (i) an exonuclease for generating complementary single strand overhang at each end, (ii) a polymerase to fill in a gap after overhangs at the ends hybridize to each other, and (iii) a ligase to seal a nick.

8. The method of claim 1, before the sequencing step further comprising fragmenting the circular dsDNA molecule to generate fragments of a pre-determined size, and selecting fragments containing the two end segments.

9. The method of claim 8, wherein the method prior to the sequencing step further includes hybridizing to the joined section with a biotin labeled probe that is complementary to the joined section and isolating the fragment that contains the joined section using streptavidin beads.

10. The method of claim 1, before the sequencing step further comprising amplifying the joined section to generate amplicons.

11. The method of claim 10, wherein the amplification is conducted with a forwarding primer annealing to immediately upstream of the 3' end fragment (3' in the original linear version), and a reverse primer anneal to immediately downstream of the 5' end fragment (5' in the original linear version).

12. The method of claim 11, wherein the forward primer or the reverse primer has a tag sequence at the 5' end.

13. The method of claim 10, wherein the amplicons are directly sequenced.

14. The method of claim 1, further comprising the amplifying the circular dsDNA molecule by rolling circle amplification (RCA).

15. The method of claim 14, wherein the RCA is carried out by Phi29 in presence of dNTP and random hexamer or specific primers.

16. The method of claim 1, wherein one or more labeled nucleotide triphosphates is incorporated into the junction in the circular dsDNA molecule.

17. The method of claim 16, wherein one or more Biotin-dUTPs are incorporated at the junction.

18. The method of claim 17, comprising selecting sections labeled with biotin.

19. The method of claim 1, wherein the sequencing step is conducted by a solid phase pyrosequencing method.

* * * * *

SEQUENCE LISTING

```
<160> NUMBER OF SEQ ID NOS: 13

<210> SEQ ID NO 1
<211> LENGTH: 25
<212> TYPE: DNA
<213> ORGANISM: Artificial Sequence
<220> FEATURE:
<223> OTHER INFORMATION: adaptor

<400> SEQUENCE: 1
ctgtctcgta acttcgcgaa gttac                                          25

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gcagccactg gtaacaggat                                                20

<210> SEQ ID NO 3
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(2)
<223> OTHER INFORMATION: n is a, c, g, or t

<400> SEQUENCE: 3
nngaacgcgc gaccctgagc t                                              21

<210> SEQ ID NO 4
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t

<400> SEQUENCE: 4
nggtgaacgt gctaccatca actgc                                          25

<210> SEQ ID NO 5
<211> LENGTH: 18
<212> TYPE: DNA
<213> ORGANISM: Artificial Sequence
<220> FEATURE:
<223> OTHER INFORMATION: primer
```

```
<220> FEATURE:
<221> NAME/KEY: misc_feature
<222> LOCATION: (1)..(2)
<223> OTHER INFORMATION: n is a, c, g, or t

<400> SEQUENCE: 5
nngaacgcgc gaccctga                                                    18

<210> SEQ ID NO 6
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t

<400> SEQUENCE: 6
nggcgatcgc gtaactatca cttgt                                            25

<210> SEQ ID NO 7
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(2)
<223> OTHER INFORMATION: n is a, c, g, or t

<400> SEQUENCE: 7
nnacggtcac cagggtgccc t                                                21

<210> SEQ ID NO 8
<211> LENGTH: 33
<212> TYPE: DNA
<213> ORGANISM: Artificial Sequence
<220> FEATURE:
<223> OTHER INFORMATION: P5 adaptor

<400> SEQUENCE: 8
acactctttc cctacacgac gctcttccga tct                                   33

<210> SEQ ID NO 9
<211> LENGTH: 32
<212> TYPE: DNA
<213> ORGANISM: Artificial Sequence
<220> FEATURE:
<223> OTHER INFORMATION: P7 adaptor

<400> SEQUENCE: 9
gactggagtt cagacgtgtg ctcttccgat ct                                    32

<210> SEQ ID NO 10
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (33)..(35)
<223> OTHER INFORMATION: n is a, c, g, or t
```

<400> SEQUENCE: 10
gactggagtt cagacgtgtg ctcttccgat ctnnntgacg atttcacgtc tggag     55

<210> SEQ ID NO 11
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (34)..(36)
<223> OTHER INFORMATION: n is a, c, g, or t

<400> SEQUENCE: 11
acactctttc cctacacgac gctcttccga tctnnncagg gtaccttgac cccagt     56

<210> SEQ ID NO 12
<211> LENGTH: 900
<212> TYPE: DNA
<213> ORGANISM: Artificial Sequence
<220> FEATURE:
<223> OTHER INFORMATION: circularized for sequencing

<400> SEQUENCE: 12
tcacaaaaat cgacgctcaa gtcagaggtg gcgaaacccg acaggactat aaagatacca     60
ggcgtttccc cctggaagct ccctcgtgcg ctctcctgtt ccgaccctgc cgcttaccgg    120
atacctgtcc gcctttctcc cttcgggaag cgtggcgctt tctcatagct cacgctgtag    180
gtatctcagt tcggtgtagg tcgttcgctc caagctgggc tgtgtgcacg aaccccccgt    240
tcagcccgac cgctgcgcct tatccggtaa ctatcgtctt gagtccaacc cggtaagaca    300
cgacttatcg ccactggcag cagccactgg taacaggatt agcagagcga ggtatgtagg    360
cggtgctaca gagttcttga agtggtggcc taactacggc tacactagaa gaacagtatt    420
tggtatctgc gctctgctga agccagttac cttcggaaaa agagttggta gctcttgatc    480
cggcaaacaa accaccgctg gtagcggtgg tttttttgtt tgcaagcagc agattacgcg    540
cagaaaaaaa ggatctcaag aagatccttt gatcttttct acggggtctg acgctcagtg    600
gaacgaaaac tcacgttaag ggattttggt catgagatta tcaaaaagga tcttcaccta    660
gatcctttta aattaaaaat gaagttttaa atcaatctaa agtatatatg agtaaacttg    720
gtctgacagt taccaatgct taatcagtga ggcacctatc tcagcgatct gtctatttcg    780
ttcatccata gttgcctgac tccccgtcgt gtagataact acgatacggg agggcttacc    840
atctggcccc agtgctgcaa tgataccgcg agacccacgc tcaccggctc cagatttatc    900

<210> SEQ ID NO 13
<211> LENGTH: 77
<212> TYPE: DNA
<213> ORGANISM: Artificial Sequence
<220> FEATURE:
<223> OTHER INFORMATION: junction region

<400> SEQUENCE: 13
ctcaccggct ccagatttat cctgtctcgt aacttcgcga agttacgaga cagtcacaaa     60
aatcgacgct caagtca                                                    77